(12) United States Patent
Sia et al.

(10) Patent No.: US 7,105,164 B1
(45) Date of Patent: Sep. 12, 2006

(54) HIV-SPECIFIC CYTOTOXIC T-CELL RESPONSES

(75) Inventors: Charles D. Y. Sia, Thornhill (CA); Pele Chong, Richmond Hill (CA); Michel H. Klein, Willowdale (CA)

(73) Assignee: Sanofi Pasteur Limited, Toronto (CA)

( * ) Notice: Subject to any disclaimer, the term of this patent is extended or adjusted under 35 U.S.C. 154(b) by 0 days.

(21) Appl. No.: 09/647,981

(22) PCT Filed: Apr. 7, 1999
(Under 37 CFR 1.47)

(86) PCT No.: PCT/CA99/00287

§ 371 (c)(1),
(2), (4) Date: May 7, 2001

(87) PCT Pub. No.: WO99/51267

PCT Pub. Date: Oct. 14, 1999

(51) Int. Cl.
*A61K 39/21* (2006.01)

(52) U.S. Cl. .................. 424/188.1; 424/208.1

(58) Field of Classification Search ............. 424/188.1, 424/208.1; 435/5
See application file for complete search history.

(56) References Cited

U.S. PATENT DOCUMENTS

| | | | | |
|---|---|---|---|---|
| 4,882,145 A | * | 11/1989 | Thornton et al. | 424/189.1 |
| 5,639,854 A | | 6/1997 | Sia et al. | 530/324 |
| 5,840,303 A | * | 11/1998 | Chisari et al. | 424/152.1 |
| 6,024,965 A | * | 2/2000 | van Baalen et al. | 424/208.1 |

FOREIGN PATENT DOCUMENTS

| EP | 470 980 B1 | 5/1990 |
|---|---|---|
| EP | 534 615 A2 | 8/1992 |
| EP | 534 618 A2 | 8/1992 |
| EP | 470 980 B1 | 3/1994 |
| WO | WO 98/22317 | 8/1995 |
| WO | WO 95/34308 | 12/1995 |
| WO | WO 96/12733 | 5/1996 |

OTHER PUBLICATIONS

Blazevic V., Ranki A., Krohn J.E.K., AIDS Research & Human Retrovirus vol. 11, (11) 1995, pp. 1335-1342.
Blazevic V. et al., Journal or Acquired Immune Deficiency Syndromes 6:881-890, 1995.
Schonbach Christian et al. Virology 226, 102-112 (1996).
Deprez B. et al., Vaccine 1996, vol. 14, No. 5 pp. 375-382.
Haynes F. B., Putman B. S., Weinberg B. J., The Finnish Medical Society DOUCECIM, Ann Med' 28, 1996, pp. 39-41.
Ian A Wilson and David H Fremont. Seminars in Immunology, vol. 5, pp. 75-80, 1993.
Kirsten Falk and Olaf Rotzschke. Seminars in Immunolgy, vol. 5, pp. 81-94, 1993.
Victor H Engelhard. Current Opinion in Immunology, vol. 6, pp. 13-23, 1994.
Salter R D and Creswell P. EMBO J., vol. 5, pp. 943, 1986.
Townsend A. et al. Nature, vol. 340, pp. 443, 1989.
Yuping Deng et al. Journal of Immunology, vol. 158, pp. 1507-1515, 1997.
Van Baalen et al. Human Immunodeficiency virus type. vol. 78, No. 8, Aug. 1997 1913-1918.
Fahey J.L.& Schooley R. Clin. exp. Immunol (1992) 88, 1-5.
Fox L. Jeffrey, No winners against AIDS, Bio/Technology vol. 12 (1994) p. 128.

* cited by examiner

*Primary Examiner*—J. S. Parkin
(74) *Attorney, Agent, or Firm*—Michael I. Stewart; Sim & McBurney

(57) ABSTRACT

A method of generating an HIV-specific cytotoxic T-cell response in a host involves an initial administration of a T-helper molecule to the host to prime T-helper cells of the immune system of the host and a subsequent administration to the host of a mixture of the T-helper molecule and a T-cell inducing HIV-derived molecule to generate an HIV-specific T-cell response in the host.

3 Claims, 9 Drawing Sheets

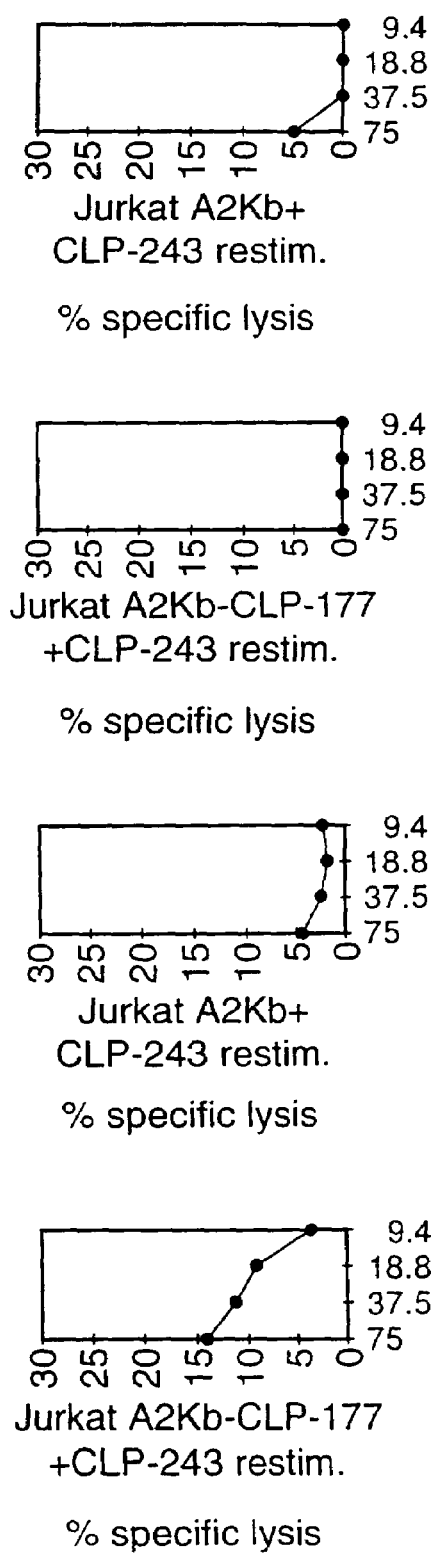

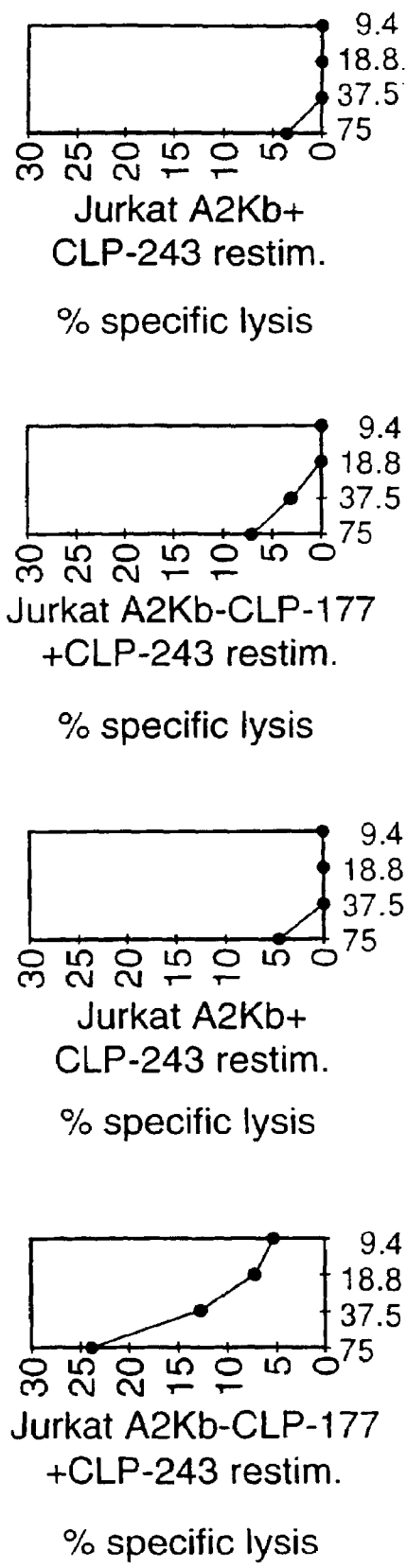

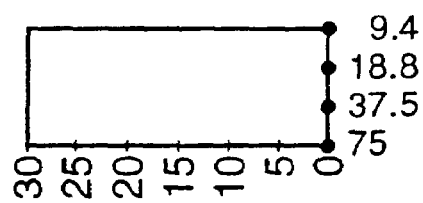
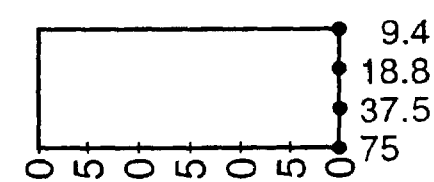
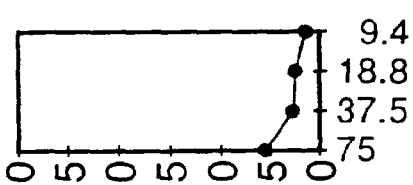
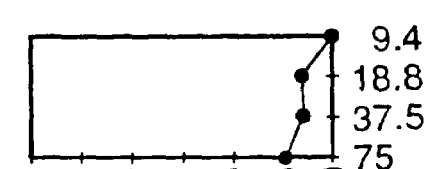

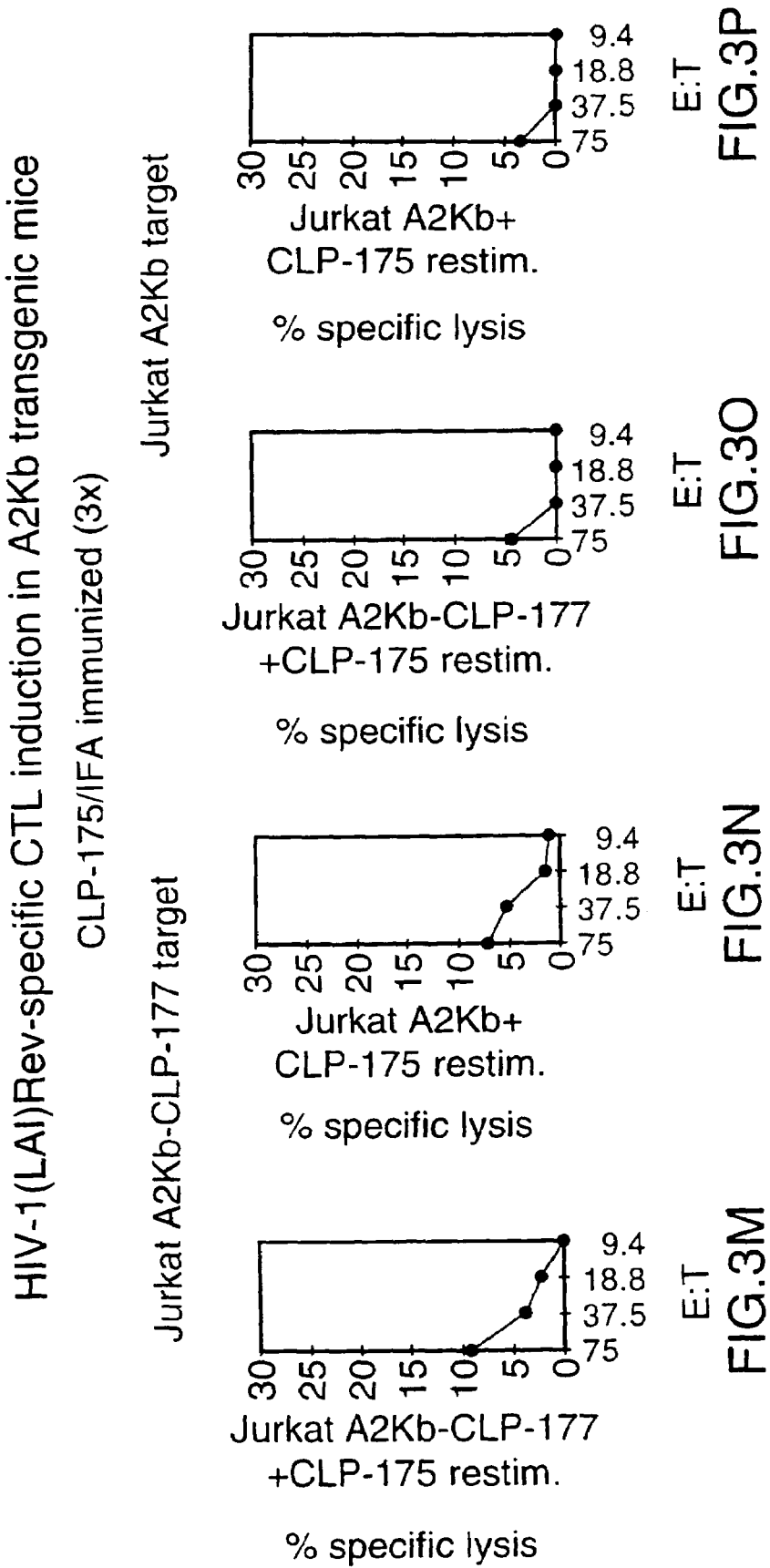

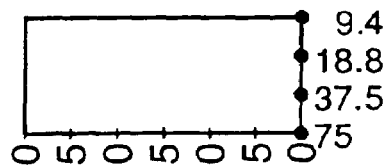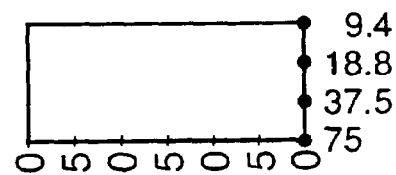

SEQUENCE LISTING

```
<160> NUMBER OF SEQ ID NOS: 10

<210> SEQ ID NO 1
<211> LENGTH: 8
<212> TYPE: PRT
<213> ORGANISM: Human immunodeficiency virus type 1

<400> SEQUENCE: 1

Asp Leu Ile Lys Ala Val Arg Leu
 1               5

<210> SEQ ID NO 2
<211> LENGTH: 9
<212> TYPE: PRT
<213> ORGANISM: Human immunodeficiency virus type 1

<400> SEQUENCE: 2

Tyr Leu Gly Arg Ser Ala Glu Pro Val
 1               5

<210> SEQ ID NO 3
<211> LENGTH: 11
<212> TYPE: PRT
<213> ORGANISM: Human immunodeficiency virus type 1

<400> SEQUENCE: 3

Tyr Leu Gly Arg Ser Ala Glu Pro Val Pro Leu
 1               5                  10

<210> SEQ ID NO 4
<211> LENGTH: 8
<212> TYPE: PRT
<213> ORGANISM: Human immunodeficiency virus type 1

<400> SEQUENCE: 4

Gln Leu Pro Pro Leu Glu Arg Leu
 1               5

<210> SEQ ID NO 5
```

-continued

```
<211> LENGTH: 10
<212> TYPE: PRT
<213> ORGANISM: Human immunodeficiency virus type 1

<400> SEQUENCE: 5

Gln Leu Pro Pro Leu Glu Arg Leu Ile Leu
 1               5                  10

<210> SEQ ID NO 6
<211> LENGTH: 10
<212> TYPE: PRT
<213> ORGANISM: Human immunodeficiency virus type 1

<400> SEQUENCE: 6

Pro Leu Gln Leu Pro Pro Leu Glu Arg Leu
 1               5                  10

<210> SEQ ID NO 7
<211> LENGTH: 12
<212> TYPE: PRT
<213> ORGANISM: Human immunodeficiency virus type 1

<400> SEQUENCE: 7

Pro Leu Gln Leu Pro Pro Leu Glu Arg Leu Ile Leu
 1               5                  10

<210> SEQ ID NO 8
<211> LENGTH: 9
<212> TYPE: PRT
<213> ORGANISM: Human immunodeficiency virus type 1

<400> SEQUENCE: 8

Ile Leu Val Glu Ser Pro Ala Val Leu
 1               5

<210> SEQ ID NO 9
<211> LENGTH: 67
<212> TYPE: PRT
<213> ORGANISM: Human immunodeficiency virus type 1

<400> SEQUENCE: 9

Arg Gln Ile His Ser Ile Ser Glu Arg Ile Leu Ser Thr Tyr Leu Gly
 1               5                  10                  15

Arg Ser Ala Glu Pro Val Pro Leu Gln Leu Pro Pro Leu Glu Arg Leu
                20                  25                  30

Thr Leu Asp Cys Asn Glu Asp Cys Gly Thr Ser Gly Thr Gln Gly Val
            35                  40                  45

Gly Ser Pro Gln Ile Leu Val Glu Ser Pro Ala Val Leu Glu Ser Gly
        50                  55                  60

Thr Lys Glu
 65

<210> SEQ ID NO 10
<211> LENGTH: 13
<212> TYPE: PRT
<213> ORGANISM: Human immunodeficiency virus type 1

<400> SEQUENCE: 10

Thr Pro Pro Ala Tyr Arg Pro Pro Asn Ala Pro Ile Leu
 1               5                  10
```

HIV-SPECIFIC CYTOTOXIC T-CELL RESPONSES

REFERENCE TO RELATED APPLICATIONS

This application is a national phase application under 35 U.S.C. 371 of PCT/CA99/00287.

FIELD OF INVENTION

The present invention relates to immunology and, in particular, to generating an HIV-specific T-cell response in a host.

BACKGROUND OF THE INVENTION

Acquired immunodeficiency syndrome (AIDS) is a disease which is the ultimate result of infection with human immunodeficiency virus (HIV). Currently, there is no effective vaccine which can protect the human population from HIV infection and hence the development of an efficacious HIV-vaccine and protocol for administering the same is urgently required. Previously, HIV-1 particles exhaustively inactivated by chemical treatments, a vaccinia vector encoding the whole envelope protein (gp160) of HIV-1, and purified recombinant gp120 have been evaluated as candidate HIV vaccines. Although inactivated HIV-1 virus preparations elicited a T-cell-mediated Delayed-Type Hypersensitivity (DTH) reaction in humans, and vaccinia/gp160 and gp120 recombinant vaccine candidates induced virus neutralizing antibodies, none of these immunogens have been shown to be efficacious human HIV vaccines. The inventors' interest in HIV vaccinology is to develop synthetic HIV-1 peptide vaccines and consider that their use alone or in conjunction with other HIV-1 vaccine candidates may lead to the elicitation of more effective immune responses against HIV-1.

The inventors' had previously described in their granted U.S. Pat. No. 5,817,318 (European Patent No. 470,980) and U.S. Pat. No. 5,639,854, the disclosures of which are incorporated herein by reference, inter alia, the identification and characterization of a T-cell epitope of the core protein, p24E, of HIV-1, and its usage in the construction of immunogenic synthetic chimeric peptides comprising p24E linked to amino acid sequences of different B-cell epitopes of an envelope or core protein of HIV-1.

The present effort has turned to the design of HIV vaccines capable of eliciting cell-mediated immunity (CMI) and protocols for the use thereof. In this context, the inventors have focused interest on a viral protein, Rev, expressed early during the life cycle of the HIV-virus, for the reason that the carboxyl terminal half is rich in human cytotoxic T-cell (CTL) motifs. Peptides which are generated via immunization with an appropriately constructed vaccine containing the Rev protein, therefore, may be presented in the context of the Major Histocompatibility Complex (MHC) class 1 molecules to induce CTL effector responses capable of killing virus infected cells early to limit virus spread. However, the immunization protocol provided herein is applicable to T-cell epitope containing peptides derived from other HIV proteins.

SUMMARY OF THE INVENTION

In accordance with one aspect of the present invention, there is provided a method of generating an HIV-specific cytotoxic T-cell (CTL) response in a host, which comprises:

administering to the host a T-helper molecule to prime T-helper cells of the immune system of the host, and subsequently administering to the host a mixture of said T-helper molecule and a T-cell inducing HIV-derived molecule to generate an HIV-specific T-cell response in the host.

Accordingly, the immune system of the host, which may be a human host, is primed by any convenient T-helper molecule and then there is subsequently administered the T-helper molecule in admixture with a T-cell inducing molecule. In this way, an HIV-specific T-cell response is obtained.

The T-helper molecule may be any of the materials well known to provide such MHC class II-helper activity in the immune system, including T-cell human DP, DR, DQ-specific T-cell epitopes. The material used as the T-helper molecule in the experimentation described herein is a peptide which corresponds to a portion of the hepatitis B virus nucleocapsid antigen, identified as CLP-243 (SEQ ID NO: 10). The T-helper molecule may be administered with an adjuvant, if desired.

The T-cell inducing HIV-derived molecule generally includes a peptide corresponding to a portion of a HIV-1 antigen and containing at least one T-cell epitope. In particular, the peptides may correspond to sequences of the Rev protein of HIV-1, particularly corresponding to amino acids 52 to 116 (SEQ ID NO:9) (Table 2) of HIV-1 (LAI) Rev (CLP-164). The amino acid sequence of Rev protein is that of the LAI isolate. The invention includes the use of corresponding peptide sequences from Rev proteins from other HIV-1 isolates, including primary isolates.

In the experimentation described herein, the peptide was effective in the protocol described herein when provided in the form of a lipopeptide, particularly when the lipid is palmitoyl or cholesterol. Two particular lipopeptides used herein are CLP-175 and CLP-176 being the palmitoyl and cholesterol derivatives, respectively, of CLP-164.

The mixtures of the T-helper molecule and T-cell inducing HIV-derived molecule may be administered with a suitable adjuvant.

The present invention further provides, in another aspect, certain novel peptides derived from the Rev protein of HIV-1. Accordingly, in this aspect of the invention, there is provided a peptide having an amino acid sequence corresponding to amino acids 52 to 116 (SEQ ID NO:9) of the sequence of the Rev protein of HIV and containing T-cell epitopes within amino acids 65 to 75 (SEQ ID NO:3), 78 to 87 (SEQ ID NO:5) and 102 to 110 (SEQ ID NO:8) (Table 1). Such peptide may be provided in the form of a lipopeptide including CLP-175 or CLP-176. The specific amino acid sequences of the peptide having SEQ ID NO:9 is that for the LAI isolate of HIV-1. Included within the scope of the invention is the corresponding peptide and corresponding T-cell epitope sequences of the Rev protein of other HIV-1 isolates, including primary isolates.

Advantages of the present invention include:

an immunization procedure to induce a T-cell response in a host immunogenic peptides for use in such procedure.

DETAILED DESCRIPTION OF INVENTION

Figure 1:
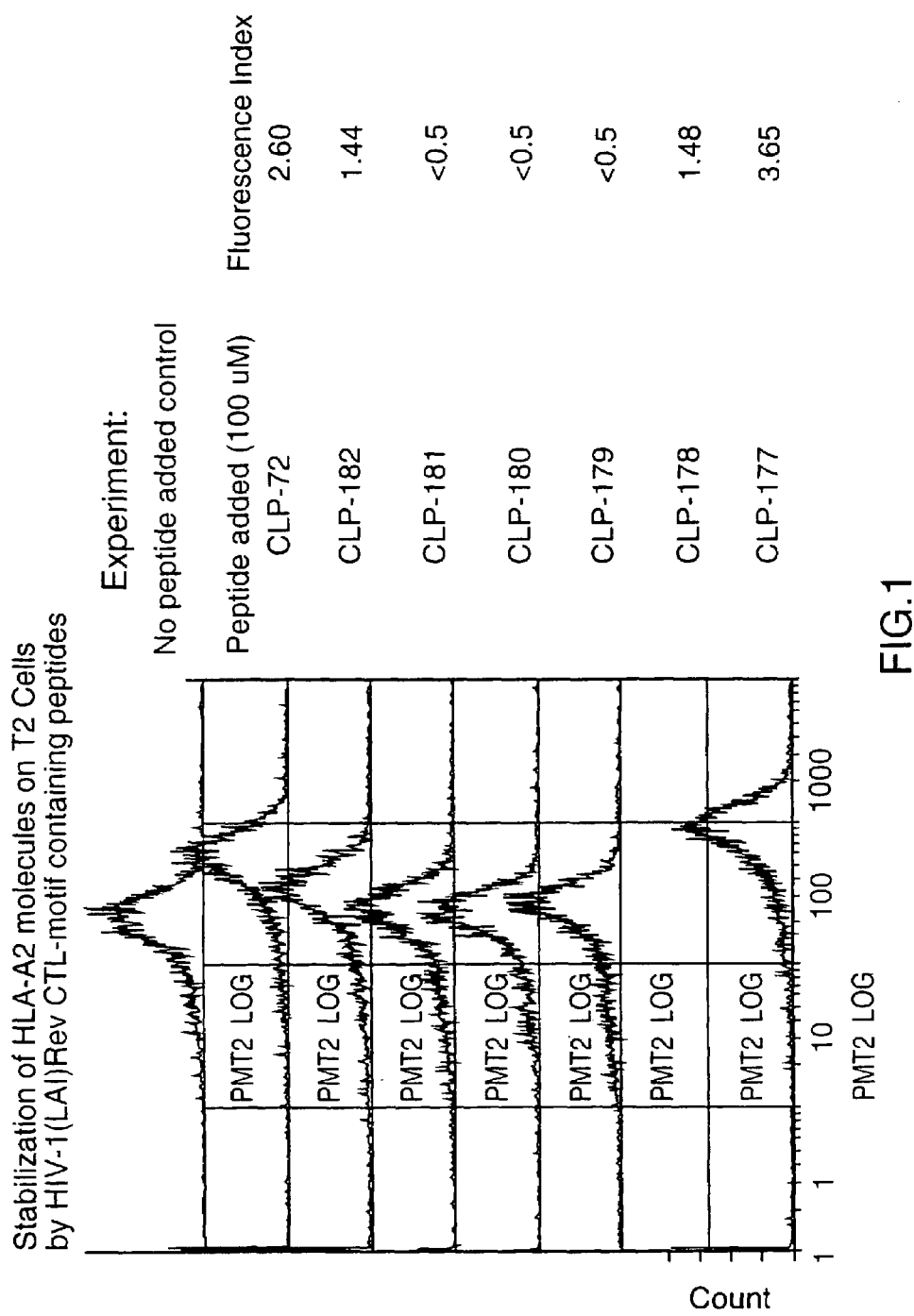
FIG. 1 illustrates the results of in vitro HLA-A2 stabilization experiments conducted using certain Rev-derived peptides by FACS (fluorescent antibody cell sorting). Peptide CLP-72 (SEQ ID NO:8), CLP-182 (SEQ ID NO:7), CLP-178 (SEQ ID NO:3) and CLP-177 (SEQ ID NO:2) bound to HLA-A2 on T2 cells are shown by shifting of the respective fluorescent peaks.
Figure 2A:
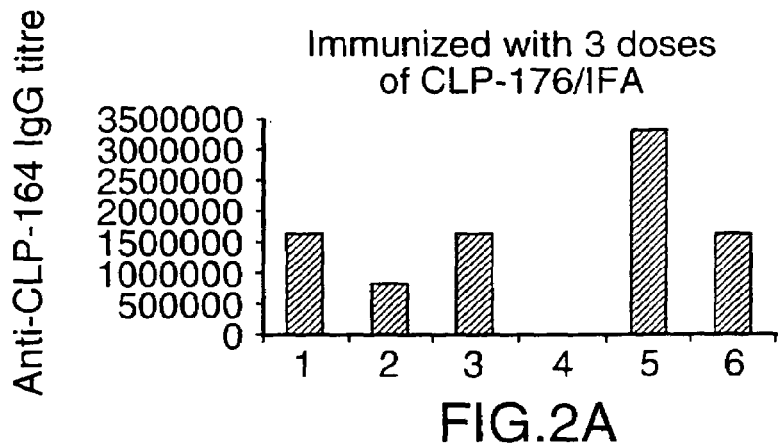
FIG. 2, comprising panels A to F, illustrates the immunogenicity of HIV-1 (LAI) Rev immunogens in A2 Kb transgenic mice using CLP-175, 176 and 164 (SEQ ID NO:9), with or without priming with CLP-243 (SEQ ID NO:10).
Figure 2B:
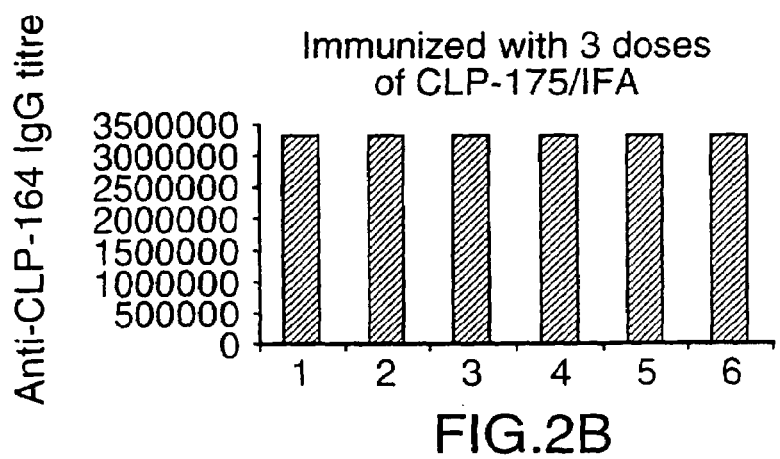
Figure 2C:
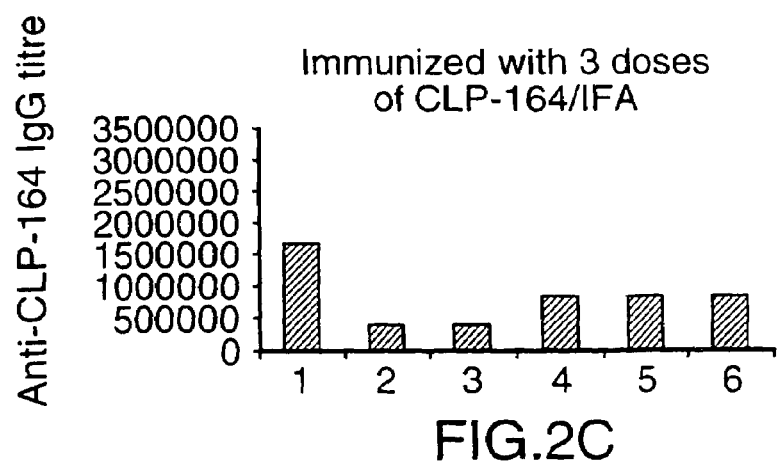
Figure 2D:
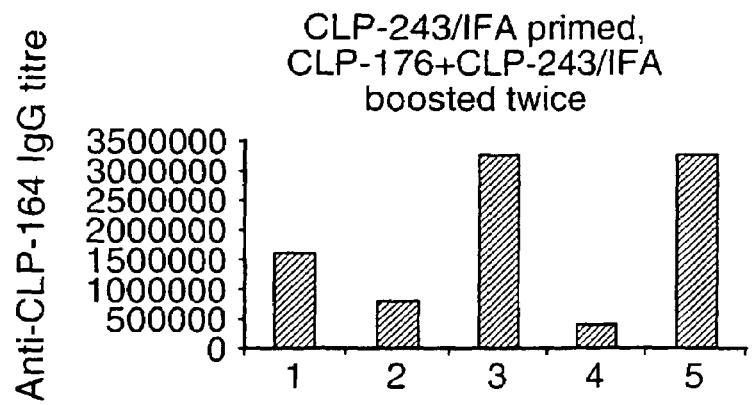
Figure 2E:
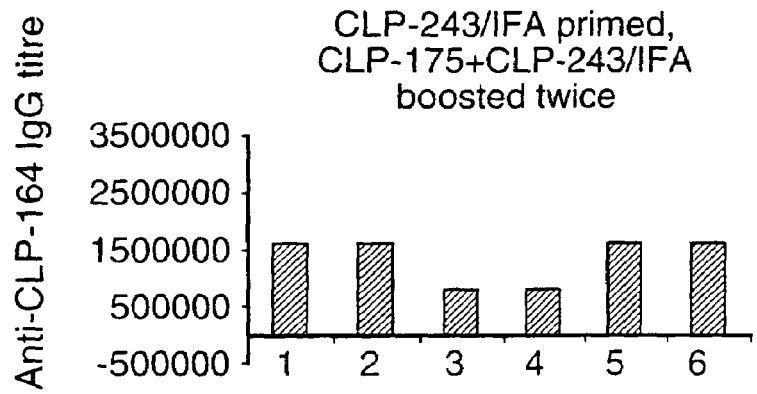
Figure 2F:
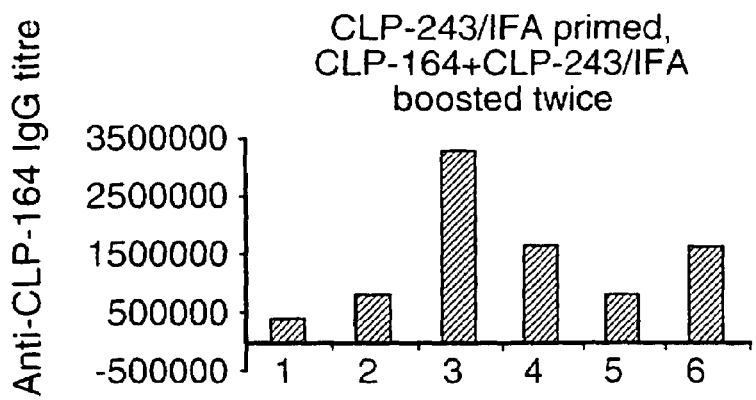
Figure 3X:
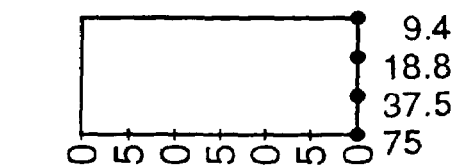
FIG. 3, comprising panels A to X, illustrates the HIV-1 (LAI) Rev-specific CTL induction in A2 Kb transgenic mice employing various protocols as described below.
Figure 3W:
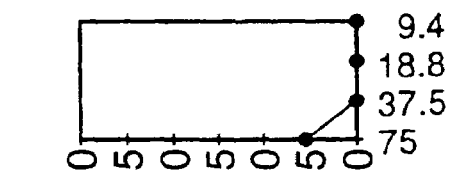
Figure 3V:
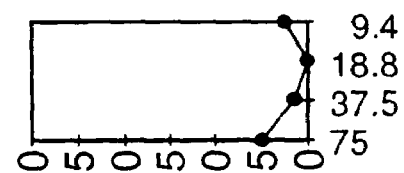
Figure 3U:
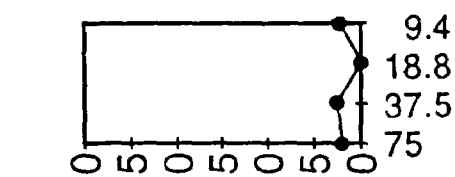

The inventors have found that two nanomer peptides, designated CLP-177 (SEQ ID NO:2) and CLP-72 (SEQ ID NO:8), a hexamer designated CLP-178 (SEQ ID NO:3), and a 12-mer designated CLP-182 (SEQ ID NO:7) of the HIV-1 (LAI) Rev protein (the amino acid sequences of the respective peptides appear in Table 1), were individually able to bind and stabilize membrane-bound Human Major Histocompatibility Complex (HLA) class 1 molecules, HLA-A2, which is the predominant HLA class 1 subtype found in caucacians. The inventors have also found that a long peptide (SEQ ID NO:9), encompassing the amino acid residues 52 to 116 of the HIV-1 (LAI) Rev protein, and constructed by having a single cholesterol or palmitoyl moiety attached to its amino-(N-) terminus via a KSS linker to form lipopeptides, CLP-176 and CLP-175 respectively, is also capable of eliciting CTL as well as antibody responses in HLA-A2 transgenic mice.

On the basis of the experimentation provided herein, there is provided hereby a novel immunization protocol for inducing a HIV-specific cytotoxic T-cell response in a host by initial administration of a T-helper molecule to prime the immune system of the host followed by administration of a mixture of the T-helper molecule and a T-cell epitope-containing peptide corresponding to a portion of an HIV antigen.

The invention is illustrated herein by using, as the T-helper molecule, a peptide which corresponds to a portion of the hepatitus B virus nucleocapsid antigen. However, other T-helper molecules may be employed, such as those providing MHC class II-helper activity in the immune system.

The invention is illustrated herein by using, as the HIV T-cell epitope containing peptide, certain lipopeptides derived from the Rev protein. However, HIV T-cell epitope containing peptides derived from any other HIV proteins may be employed.

One model has recently been used to predict human CTL antigenic determinants on the basis of the primary sequence (see references 1 to 3, throughout this specification, various references are referred to in parenthesis to more fully describe the state of the art to which this invention pertains. Full bibliographic information for each citation is found at the end of the specification, immediately following the claims. The disclosures of these references are hereby incorporated by reference into the present disclosure). It has been proposed that CTL epitopes which are most favoured to bind and lodge into the peptide-binding groove of the human MHC class 1 molecule, such as HLA-A2, is usually 9 amino acids long. However, peptides containing 8 to 13 amino acids able to interact with HLA class 1 molecules have also been reported. In the majority of cases, these peptides are found to contain a leucine (L) or methionine (M) residue at position 2, and either L or valine (V) at their carboxy-terminal ends.

Location of the potential CTL containing motifs of the HIV-1 (LAI) Rev protein has been predicted by the reported peptide-binding motif algorithms. Table 1 shows the amino acid sequences of such predicted peptides (SEQ ID NOS: 1 to 8). The ability of the peptides containing these motifs to bind and stabilize membrane-bound HLA-A2 molecule was assessed using the T2 cell line. The cell line has been well documented to have defective TAP transporter function resulting in the majority of the intracellularly generated peptides being unable to be transported into the endoplasmic reticulum to associate with the newly synthesized HLA class 1 molecules, i.e. HLA-A2 (see references 4, 5). The majority of the HLA-A2 molecules displayed on the surface of the T2 cells are, therefore, empty (i.e. contain no peptides) and are unstable. Upon interaction with suitable peptides introduced exogenously, the stability of the HLA-A2 molecules can be restored.

The results of in vitro HLA-A2 stabilization experiments conducted herein demonstrated that two nanomers, namely, CLP-177 (SEQ ID NO:2) and CLP-72 (SEQ ID NO:8); and a 11-mer and a 12-mer represented by the peptides, namely CLP-178 (SEQ ID NO:3) and CLP-182 (SEQ ID NO:4) respectively; were capable of binding to HLA-A2 on T2 cells. This result was shown by shifting of the respective fluorescent peaks to the right due to higher density of class 1 molecules displayed on the cells, as shown in accompanying FIG. 1. A comparison of the respective fluorescence indices revealed that the potency of the peptides is in the order of CLP-177>CLP-72>CLP-178>CLP-182.

The constructions of lipidated Rev peptides which were tested are shown in Table 2. The results depicted in FIG. 2 illustrate that lipidated Rev 52 to 116 (SEQ ID NO:9) peptides, CLP-175 and CLP-176; as well as their non-lipidated counterpart, CLP-164, were immunogenic, as determined by IgG titre, when injected three times at a dose of 100.0 µg into the A2 Kb transgenic mice (ref. 6). High IgG antibodies directed against the Rev 52 to 116 peptide (CLP-164) were detected in animals administered with Incomplete Freund's Adjuvant (IFA)-formulated CLP-175, or CLP-176 or CLP-164 (Panels A, B and C). Mice tested under a different experimental setting by priming them with a dose of CLP-243 in IFA, followed by boosting twice with a mixture of IFA-formulated CLP-243+CLP-175, or CLP-243+CLP-176 or CLP-243+CLP-164, similarly elicited a high anti-CLP-164 antibody response (Panels D to F). CLP-243 is an I-A$^b$-restricted peptide encompassing the amino acids residues 128 to 140 (TPPAYRPPNAPIL; SEQ ID NO:10) of the hepatitus B virus nucleocapsid antigen (ref. 6).

The results of the immunogenicity experiments demonstrating that the lipopeptides, CLP-176 and CLP-175, were CTL-inducing are shown in FIG. 3. A2 Kb transgenic mice primed subcutaneously with a dose of the I-A$^b$-restricted peptide, CLP-243 in IFA, and boosted twice using the same immunization route with a mixture of the priming dose of CLP-243 and either 100.0 µg of CLP-176 or CLP-175 in IFA were found to generate effector cells killing the Jurkat-A2 Kb target cells pulsed with the nanomer, CLP-177 (Panels A, B, E, F). The cytotoxic activity of the effectors were specific because Jurkat A2 Kb cells not loaded with CLP-177 were not killed (Panels C, D, G and H). In contrast, the A2 Kb transgenic animals injected similarly once with the CLP- 243/IFA inoculum, then twice with CLP-243 plus CLP-164 in IFA, failed to elicit a significant CLP-177-specific effector response (Panels I, J, K, L).

The results of immunization experiments demonstrating that priming with the I-A$^b$-restricted peptide, CLP-243, followed by boosting with a mixture of CLP-243 and CLP-176 or CLP-175, was more effective than immunization with the respective lipopeptide alone for the induction of CTL response are shown in FIG. 3. It was found that splenocytes of A2 Kb transgenic mice injected 3 times subcutaneously with a dose of 100.0 μg of CLP-176, or CLP-175, or CLP-164 (the non-lipidated Rev 52–116) in IFA, and re-stimulated with CLP-177 pulsed Jurkat A2 Kb cells and exogenously added CLP-175 at a concentration of 15.0 μg per ml did not result in the generation of effectors capable of killing Jurkat cells pulsed with the CLP-177 peptide (Panels M to X).

The results of the in vitro re-stimulation experiments showed that the simultaneous re-stimulation of the CLP-243-specific I-A$^b$-restricted T-helper cells achieved by the addition of the CLP-243 peptide, and the CLP-177-specific effectors achieved by co-culturing them with CLP-177-pulsed Jurkat A2 Kb cells was required to augment the enrichment of the CLP-177-specific effectors to allow their detection in the in vitro CTL assay.

The components are administered in a manner compatible with the dosage formulation, and in such amount as will be therapeutically effective, immunogenic and protective in the immunization protocol. The quantity of material to be administered depends on the subject to be treated, including, for example, the capacity of the immune system of the individual to synthesize antibodies, and to produce a cell-mediated immune response. Precise amounts of active ingredient required to be administered depend on the judgement of the practitioner. However, suitable dosage ranges are readily determinable by one skilled in the art and may be of the order of micrograms to miligrams of material. The dosage may also depend on the route of administration and will vary according to the size of the host.

Immunogenicity can be significantly improved if the antigens are co-administered with adjuvants. Adjuvants enhance the immunogenicity of an antigen but are not necessarily immunogenic themselves. Adjuvant may act by retaining the antigen locally near the site of administration to produce a depot effect facilitating a slow, sustained release of antigen to cells of the immune system. Adjuvants can also attract cells of the immune system to an antigen depot and stimulate such cells to elicit immune response.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in toxoids is well established and a HBsAg vaccine has been adjuvanted with alum.

A wide range of extrinsic adjuvants can provoke potent immune responses to antigens. These include aluminum phosphate, aluminum hydroxide, QS21, Quil A, derivatives and components thereof, calcium phosphate, calcium hydroxide, zinc hydroxide, a glycolipid analog, an octodecyl ester of an amino acid, a muramyl dipeptide, polyphosphazene, a lipoprotein, ISCOM matrix, DC-Chol, DDBA, and other adjuvants and bacterial toxins, components and derivatives thereof. Particularly advantageous combination are described in copending U.S. application Ser. No. 08/258,228 filed Jun. 13, 1994 and Ser. No. 08/483,856 filed Jun. 7, 1995, assigned to the assignee hereof and the disclosure of which is incorporated herein by reference thereto (WO 95/34308). Under particular circumstances adjuvants that induce a Th1 response are desirable.

The invention is further illustrated by the following Examples.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Methods of peptide and lipopeptide synthesis, cell culture, enzyme immunoassays (EIA), CTL assay and other testing procedures that are not explicitly described in this disclosure are amply reported in the scientific literature and are well within the scope of those skilled in the art.

Example 1

This Example illustrates the synthesis of peptides and lipopeptides.

Solid phase peptide syntheses were conducted on an ABI 430A automated peptide synthesizer according to the manufacturer's standard protocols. The amino acid sequences of the synthesized peptides are shown in Table 1 below.

Lysine residues designed for subsequent lipidation were incorporated into the peptides by using N$^\alpha$-t-butyloxycarbonyl-N$^\epsilon$-fluorenylmethoxycarbonyl-lysine (Boc-Lys(Fmoc)-OH). The lipid moieties were incorporated by manual removal of the side chain Fmoc protecting group followed by acylation with the appropriate carboxylic acid activated with O-benzotriazol-1-yl-N,N,N',N'-tetramethyluronium hexa-fluorophosphate (HBTU) and diisopropylethylamine in dimethylformamide (DMF). The lipopeptides were cleaved from the solid support by treatment with liquid hydrogen fluoride in a presence of thiocresole, anisole and methyl sulfide. The crude products were extracted with trifluoroacetic acid (TFA) and precipitated with diethyl ether. The lipopeptides and the unlipidated peptides are shown in Table 2.

Example 2

This Example illustrates the method used to demonstrate the HLA-A2 binding and modulation of peptides.

T2 cell line expressing the HLA-A2 molecules was obtained from Dr Peter Creswell at the Howard Hughes Research Institute of Yale University. The cells were propagated in Iscove's complete medium (Iscove's medium supplemented with 10% heat-inactivated bovine serum, 120.0 units per ml of penicilin G sodium, 120 μg per ml of streptomycin sulphate, and 0.35 mg per ml of L-glutamine). The ability of individual 8 to 13 mer peptides, prepared as described in Example 1 and identified in Table 1, to bind and modulate the stability of the A2 molecules on T2 cells was determined using a peptide-induced MHC class 1 assembly assay, which was modified from a protocol described by Yuping Deng et al. (ref. 6).

In essence, $1\times10^6$ T2 cells were incubated with a specified concentration of the test peptide in 250.0 μl of Iscove's serum-free medium (Iscove's medium supplemented with 120.0 units per ml of penicillin G sodium, 120.0 μg per ml of streptomycin sulphate and 0.35 mg per ml of L-glutamine) in a sterile Eppendorf tube at 37° C. overnight. The cells were then incubated on ice for 30 min before 1.0 ml of Iscove's complete medium supplemented with 5.0 μg per ml of brefeldin A, 12.5 μg per ml of anisomycin and 5.0 μg per ml of cyclohexamide was added. The samples were then incubated for 3.0 hr in a 37° C. $CO_2$ incubator.

In the presence of the drugs, further protein synthesis and intracellular delivery of HLA-A2 molecules to the cell surface are inhibited, and de-stabilization of the conformation of the membrane-bound class 1 molecules at the physiological temperature occurs.

The cells were then washed twice with ice-cold PBA (a buffer containing 0.9% sodium chloride, 0.5% bovine serum albumin and 0.02% sodium azide). 100.0 μl of PBA containing 5.0 μg of a conformation-sensitive HLA-A2-specific mouse monoclonal antibody, BB7.2 (ref. 7), was then added to each test sample. The reaction was allowed to take place on ice for 45 min. The cells were then washed three times with ice-cold PBA.

The binding of BB7.2 was then detected by adding 100.0 of PBA containing 1.0 μg of goat anti-mouse IgG F(ab') fluorescein (FITC) conjugate to each cell sample. After 30 min incubation on ice, the cells were washed twice with PBA, and twice again with PBS, pH 7.2. Cells were fixed immediately after washing was completed by adding 100.0 μl of 1.0% paraformaldehyde to the cell pellet. The cells were gently resuspended and were FACS analysed usually within three days after the experiments were completed.

The fluorescence index, which is an indicator for increased density of membrane-bound A2 molecules, was calculated by dividing the mean fluorescence of an experimental sample (peptide treated T2 cells) by the mean fluorescence of the control sample (T2 cells not treated with peptide). The results obtained are set forth in FIG. 1.

Example 3

This Example describes the prime and boost protocol used to test the immunogenicity of the peptides and lipopeptides.

Mice of the B1O background which were transgenic for the A2 Kb chimeric gene were purchased and licensed from the Scripps Clinic in California, USA. The colony is kept in the Animal Service Facility in Pasteur Merieux Connaught Canada.

A first group of the mice were injected subcutaneously at the base of the tail with a dose of 100.0 μg of IFA-formulated peptide or lipopeptide emulsified in IFA and were then boosted at 30 days and again at 42 to 48 days later with the same inoculum. A second group of mice were injected subcutaneously at the base of the tail with a dose of 100.0 μg of an IFA-formulated CLP-243 and were then boosted with an IFA-formulated mixture of the same dose of the priming immunogen and 100.0 μg of CLP-175, or CLP-176, or CLP-164.

Sera of the experimental animals collected on the 10th or 11th day post final-injection were assayed for CLP-164-specific IgG antibodies using a standard EIA. The results obtained are shown in FIG. 2. Splenocytes of the experimental mice were simultaneously cultured to enrich for CTLs before assaying for effector activity, as described below.

Example 4

This Example illustrates an in vitro culture method used to enrich for CTL effectors and CTL assay.

Splenocytes of the experimental A2 Kb transgenic mice from Example 3 at $3.0\times10^7$ were co-cultured with $1.3\times10^7$ A2 Kb transfected Jurkat cells pulsed with the peptides CLP-175 or CLP 176 in 15.0 ml of complete medium (RPMI 1640 supplemented with 10.0% 56° C. heat-inactivated bovine serum, 120.0 units per ml of penicillin G sodium, 120.0 μg per ml of streptomycin sulphate and 0.35 mg per ml of L-glutamine) per 25 cm² tissue culture flask. The $I-A^b$-restricted peptide, CLP-243, was also added at a concentration of 15.0 μg per ml at the initiation of the culture. The cultures were kept at 37° C. in a $CO_2$ incubator for 7 days, and the responders were then tested against peptide-pulsed Jurkat A2 Kb transfectant in a standard in vitro 4 hr CTL assay, as follows.

The responders were harvested from the 7-day cultures and washed twice with the complete medium. The positive target was created by incubating $1\times10^6$ Jurkat A2 Kb cells with 100.0 μg of the specified peptide for overnight in a 37° C. $CO_2$ incubator. The target cells were then labelled with $^{51}Cr$ at 250.0 uCi per $1\times10^6$ cells for 1.5 hr in the presence of 25.0 μg of the same test peptides. After washing twice with complete medium to remove excess of $^{51}Cr$, the targets were incubated at $2.5\times10^3$ with different numbers of the responders for 4 hr in a 37° C. $CO_2$ incubator. Half amount of the supernatant was then removed and counted for radio-activity. The results obtained are shown in FIG. 3.

SUMMARY OF THE DISCLOSURE

In summary of this disclosure, the present invention provides a novel protocol for achieving a HIV-specific CTL response in a host, including a human host, by a prime/boost procedure using T-helper molecules and lipidated peptides of HIV protein, as well as novel peptides and lipopeptides. Modifications are possible within the scope of the invention.

TABLE 1

HLA-A2-restricted CTL motifs of the HIV-1 (LAI) Rev protein

| PEPTIDE | SEQUENCE | AMINO ACIDS | SEQ ID NO: |
|---|---|---|---|
| 1. CLP-279 | DLIKAVRL | 11–18 | 1 |
| 2. CLP-177 | YLGRSAEPV | 65–73 | 2 |
| 3. CLP-178 | YLGRSAEPVPL | 65–75 | 3 |
| 4. CLP-179 | QLPPLERL | 78–85 | 4 |
| 5. CLP-180 | QLPPLERLIL | 78–87 | 5 |
| 6. CLP-181 | PLQLPPLERL | 76–85 | 6 |
| 7. CLP-182 | PLQLPPLERLIL | 76–87 | 7 |
| 8. CLP-72 | ILVESPAVL | 102–110 | 8 |

TABLE 2

HIV-1 (LAI) Rev 52–116 lipopeptides/peptide tested

| Lipopeptide/peptide | | Construction |
|---|---|---|
| CLP-175 | K[Palmitoyl] | SS-RQIHSISERILSTYLGRSAEPVPLQLPPLERLTL-DCNEDCGTSGTQGVGSPQILVESPAVLESGTKE |
| CLP-176 | K[cholesterol] | SS-RQIHSISERILSTYLGRSAEPVPLQLPPLERLTL-DCNEDCGTSGTQGVGSPQILVESPAVLESGTKE |
| CLP-164 | | RQIHSISERILSTYLGRSAEPVPLQLPPLERLTL-DCNEDCGTSGTQGVGSPQILVESPAVLESGTKE (SEQ ID NO:9) |

REFERENCES

1. Ian A Wilson and Daved H Fremont. Seminars in Immunology, Vol 5, pp 75–80, 1993.
2. Kirsten Falk and Olaf Rotzschke. Seminars in Immunology, Vol 5, pp 81–94, 1993.
3. Victor H Engelhard. Current Opinion in Immunology, Vol 6, pp 13–23, 1994.
4. Salter R D and Creswell P. EMBO J., Vol 5, pp 943, 1986.
5. Townsend A. et al. Nature, Vol 340, pp 443, 1989.
6. Yuping Deng et al. Journal of Immunology, Vol 158, pp 1507–1515, 1997.

We claim:

1. A method of generating an HIV-specific cytotoxic T-cell (CTL) response in a host, which comprises:
   administering to the host a T-helper molecule to prime T-helper cells of the immune system of the host, said T-helper molecule being CLP-243 (SEQ ID NO:10) and
   subsequently administering to the host a mixture of said T-helper molecule and a T-cell inducing HIV-derived molecule to generate an HIV-specific T-cell response in the host, said T-cell inducing HIV-derived molecule being a lipopeptide which is CLP-175 or CLP-176.

2. The method of claim 1 wherein said T-helper molecule is administered with an adjuvant.

3. The method of claim 1 wherein said mixture is administered with an adjuvant.

* * * * *